(12) United States Patent
Zhu et al.

(10) Patent No.: US 6,889,092 B2
(45) Date of Patent: May 3, 2005

(54) HIGH IMPEDANCE ELECTRODE ASSEMBLY

(75) Inventors: Qingsheng Zhu, Little Canada, MN (US); Ronald W. Heil, Jr., Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 344 days.

(21) Appl. No.: 10/034,503

(22) Filed: Dec. 28, 2001

(65) Prior Publication Data

US 2002/0058981 A1 May 16, 2002

Related U.S. Application Data

(63) Continuation of application No. 09/406,207, filed on Sep. 24, 1999, now Pat. No. 6,363,286.

(51) Int. Cl.[7] ............................................. A61N 1/05
(52) U.S. Cl. ........................................ 607/120; 607/122
(58) Field of Search ................... 607/116, 119, 607/121, 122, 123, 120

(56) References Cited

U.S. PATENT DOCUMENTS

| | | | |
|---|---|---|---|
| 3,572,344 A | 3/1971 | Bolduc | 128/418 |
| 3,788,329 A | 1/1974 | Friedman | 128/418 |
| 3,804,098 A | 4/1974 | Friedman | 128/404 |
| 3,825,015 A | 7/1974 | Berkovitz | 128/404 |
| 4,030,508 A | 6/1977 | Thalen | 128/418 |
| 4,156,429 A | 5/1979 | Amundson | 128/419 |
| 4,328,812 A | * 5/1982 | Ufford et al. | 607/122 |
| 4,393,883 A | 7/1983 | Smyth et al. | 128/785 |
| 4,444,195 A | 4/1984 | Gold | 128/642 |
| 4,458,695 A | * 7/1984 | Peers-Trevarton | 607/123 |
| 4,538,623 A | 9/1985 | Proctor et al. | 128/784 |
| 4,559,951 A | 12/1985 | Dahl et al. | 128/642 |

(Continued)

FOREIGN PATENT DOCUMENTS

| | | | |
|---|---|---|---|
| DE | 2827595 | 4/1979 | A61N/1/36 |
| EP | 0057877 | 8/1982 | 607/121 |
| EP | 0573275 | 12/1993 | A61N/1/05 |
| EP | 0612538 | 8/1994 | A61N/1/05 |
| EP | 0620024 | 10/1994 | A61N/1/05 |
| EP | 0916363 | 5/1999 | A61N/1/05 |
| GB | 2240721 | 8/1991 | A61N/1/05 |
| WO | WO-91/19533 | 6/1991 | A61N/1/05 |

OTHER PUBLICATIONS

Brownlee, R. R., "Toward Optimizing the Detection of Atrial Depolarization with Floating Bipolar Electrodes", *Pace*, vol. 12, (Mar. 1989),pp. 431–442.

(Continued)

*Primary Examiner*—George R. Evanisko
(74) *Attorney, Agent, or Firm*—Schwegman, Lundberg, Woessner & Kluth, P.A.

(57) ABSTRACT

A lead having an electrode assembly has a high impedance electrode. The high impedance electrode includes a partially insulated sleeve electrode or a wire filament. The high impedance electrode includes an exposed surface of less than 1.2 mm$^2$. One or more eluting drugs are disposed adjacent to the high impedance electrode.

20 Claims, 5 Drawing Sheets

U.S. PATENT DOCUMENTS

| | | | |
|---|---|---|---|
| 4,592,372 A | 6/1986 | Beranek | 128/786 |
| 4,633,880 A | 1/1987 | Osypka et al. | 128/642 |
| 4,649,937 A | 3/1987 | DeHaan et al. | 128/784 |
| 4,679,572 A | 7/1987 | Baker, Jr. | 128/786 |
| 4,784,161 A | 11/1988 | Skalsky et al. | 128/785 |
| 4,819,661 A | 4/1989 | Heil, Jr. et al. | 128/786 |
| 4,819,662 A | 4/1989 | Heil, Jr. et al. | 128/786 |
| 5,016,646 A | 5/1991 | Gotthardt et al. | 128/784 |
| 5,063,932 A | 11/1991 | Dahl et al. | 128/639 |
| 5,127,403 A * | 7/1992 | Brownlee | 607/122 |
| 5,172,694 A | 12/1992 | Flammang et al. | 128/642 |
| 5,230,337 A | 7/1993 | Dahl et al. | 607/5 |
| 5,265,601 A | 11/1993 | Mehra | 607/9 |
| 5,324,327 A | 6/1994 | Cohen | 607/122 |
| 5,342,407 A | 8/1994 | Dahl et al. | 607/129 |
| 5,354,327 A | 10/1994 | Smits | 607/116 |
| 5,360,442 A | 11/1994 | Dahl et al. | 607/129 |
| 5,405,373 A | 4/1995 | Petersson et al. | 607/121 |
| 5,408,744 A * | 4/1995 | Gates | 29/875 |
| 5,411,544 A | 5/1995 | Mar et al. | 607/122 |
| 5,476,499 A * | 12/1995 | Hirschberg | 607/123 |
| 5,545,202 A | 8/1996 | Dahl et al. | 607/129 |
| 5,545,205 A | 8/1996 | Schulte et al. | 607/123 |
| 5,554,178 A | 9/1996 | Dahl et al. | 607/122 |
| 5,578,068 A | 11/1996 | Laske et al. | 607/126 |
| 5,603,732 A | 2/1997 | Dahl et al. | 607/129 |
| 5,755,764 A | 5/1998 | Schroeppel | 607/122 |
| 5,769,881 A | 6/1998 | Schroeppel et al. | 607/123 |
| 5,871,529 A | 2/1999 | Bartig et al. | 607/122 |
| 5,902,330 A | 5/1999 | Ollivier et al. | 607/122 |
| 6,141,593 A | 10/2000 | Patag | 607/122 |

OTHER PUBLICATIONS

Ellenbogen, K. A., et al., "Steroid eluting high impedance pacing leads decrease short and long term current drain: results from a multicenter clinical trial", *Pace—Pacing and Clinical Electrophysiology*, vol. 22, No. 1 Part 1, XP000803901, (Jan. 1999),39–48.

Hirschberg, J., "A New Dual Chamber Single Lead System", *Pacing & Electrophysiology*, 17(11 Pt 2), (Nov. 1994), 1870–1872.

Hughes, Howard C., et al., "Simultaneous Atrial and Ventricular Electrogram Transmission Via a Specialized Single Lead System", *Pace*, vol. 7, Part II,(Nov.–Dec. 19),pp. 1195–1201.

Tarjan, P., et al., "Optimal Electrode Positions for the Bipolar Atrial Pair on a Single–Pass Atrio–Ventricular Permanent Pacing Lead", *Pace*, vol. 10, Abstract 114,(Mar.–Apr. 1987),p. 434.

* cited by examiner

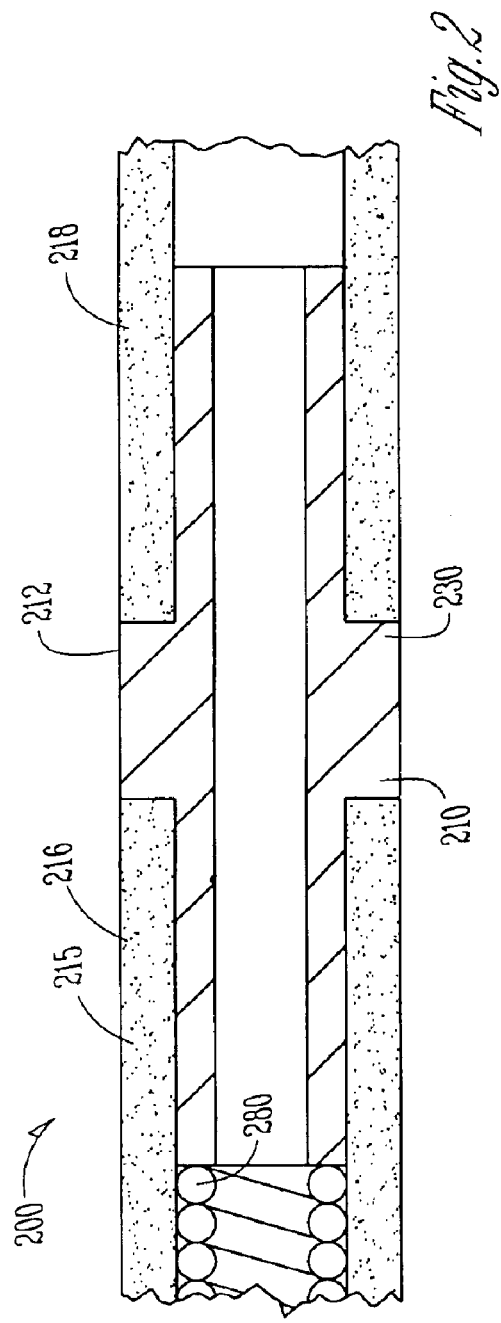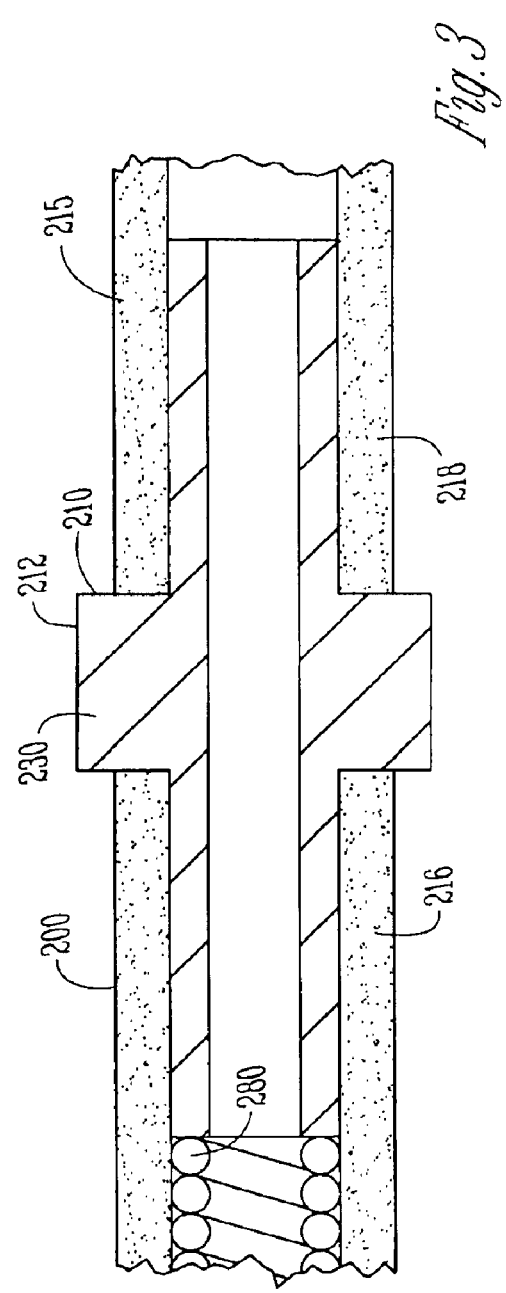

HIGH IMPEDANCE ELECTRODE ASSEMBLY

CROSS-REFERENCE TO RELATE APPLICATION(S)

This patent application is a continuation of U.S. patent application Ser. No. 09/406,207, filed on Sep. 24, 1999 now U.S. Pat. No. 6,363,286, the specification of which is hereby incorporated by reference.

This patent application is related to the foreign patent application entitled, "Electrode for High Impedance Heart Stimulation," having Ser. No. 98/00675, filed on Jan. 15, 1998 and to U.S. Pat. No. 5,871,529, filed on Jan. 16, 1997, entitled "Electrode for High Impedance Heart Stimulation," the specifications of which are hereby incorporated by reference.

FIELD OF THE INVENTION

The present invention relates generally to leads for conducting electrical signals to and from the heart. More particularly, it pertains to a high impedance electrode assembly for delivering electrical charges to and from the heart.

BACKGROUND OF THE INVENTION

Leads implanted in or about the heart have been used to reverse certain life threatening arrhythmias, or to stimulate contraction of the heart. Electrical energy is applied to the heart via the leads to return the heart to normal rhythm. Leads have also been used to sense in the atrium or ventricle of the heart and to deliver pacing pulses to the atrium or ventricle.

Cardiac pacing may be performed by the transvenous method or by leads implanted directly onto the epicardium. Permanent transvenous pacing is performed using a lead positioned within one or more chambers of the heart. A lead may be positioned in the ventricle or in the atrium through a subclavian vein, and the lead terminal pins are attached to a pacemaker which is implanted subcutaneously. The lead provides the electrical connection between the pulse generator and the heart tissue which is to be excited.

The pacemaker includes a power source for the electrical energy which is applied to the heart from the pacemaker. Since pulse generators are implanted subcutaneously within the patient, it is undesirable when excessive current drain is placed on the power source for the pacemaker. High stimulation thresholds can in result in excessive current drain from the power source. In addition, larger surface areas of electrodes require larger amounts of energy to deliver pacing pulses. A shorter battery life for a pacemaker also results increased number of medical procedures for the patient. The increased number of medical procedures result in increased risk and cost to the patient.

Accordingly, there is a need for a high impedance electrode for pacing and/or sensing the atrium and/or the ventricle. In addition, there is a need for an electrode which does not excessively drain the power source of a pacemaker.

SUMMARY OF THE INVENTION

A lead assembly includes a lead body which extends from a proximal end to a distal end. The lead body has at least one conductor and the body is defined in part by a circumference. At least one electrode is electrically coupled with the conductor, where the electrode comprises a wire filament disposed about the circumference of the lead body. The wire filament is bonded with the lead body. In one embodiment, a conductor coil is disposed within the lead body, where a portion of the conductor coil extends through the lead body and around the circumference of the lead body to form the wire filament disposed about the lead body.

In another embodiment, a lead assembly has a lead body which extends from a proximal end to a distal end and defined in part by a circumference. The lead body has a conductor coil, and an electrode assembly including at least one electrode electrically coupled with the conductor coil. The electrode comprises a conductive sleeve which is partially masked by the lead body.

The lead assembly further includes, in another embodiment, at least one drug elution collar adjacent to the electrode. In yet another embodiment, the lead assembly further includes a first drug elution collar and a second drug elution collar. The first drug elution collar and the second drug elution collar straddle the exposed electrode surface. In one embodiment, the first drug elution collar has a first drug therein, the second drug elution collar has a second drug therein, and the first drug is different than the second drug. The lead further comprises a porous member disposed on the lead body proximate to the electrode.

In yet another embodiment, the lead assembly includes an electrode having an exposed electrode surface, where the exposed electrode surface is offset from a surface of the lead body. Alternatively, the exposed electrode surface is flush with a surface of the lead body. The exposed electrode surface, in another embodiment, extends about the circumference of the lead body.

In another embodiment, a lead assembly includes a lead body which extends from a proximal end to a distal end. The lead body has a conductor coil and an electrode is electrically coupled with the conductor. The electrode has a high pacing impedance, where the electrode has a surface area less than about 1.2 mm$^2$. In one embodiment, the electrode comprises a conductive sleeve partially masked by the lead body. Optionally, at least one drug elution collar is disposed adjacent to the electrode. The drug elution collar includes a first drug elution collar and a second drug elution collar, where each collar is disposed on opposite sides of the sleeve. In one embodiment, the first drug elution collar has a first drug which is different than a second drug of the second drug elution collar. The lead assembly, in another embodiment, further includes a porous member on the lead body proximate to the electrode.

In yet another embodiment, the lead assembly includes an electrode having an exposed electrode surface, where the exposed electrode surface is offset from a surface of the lead body. Alternatively, the exposed electrode surface is flush with a surface of the lead body. The exposed electrode surface, in another embodiment, extends about the circumference of the lead body. In another embodiment, a conductor coil is disposed within the lead body, where a portion of the conductor coil extends through the lead body and around the circumference of the lead body to form the wire filament disposed about the lead body. Optionally, the wire filament is bonded with the lead body.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 2 is a cross-section of an electrode assembly constructed in accordance with one embodiment.

FIG. 3 is a cross-section of an electrode assembly constructed in accordance with one embodiment.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1A:
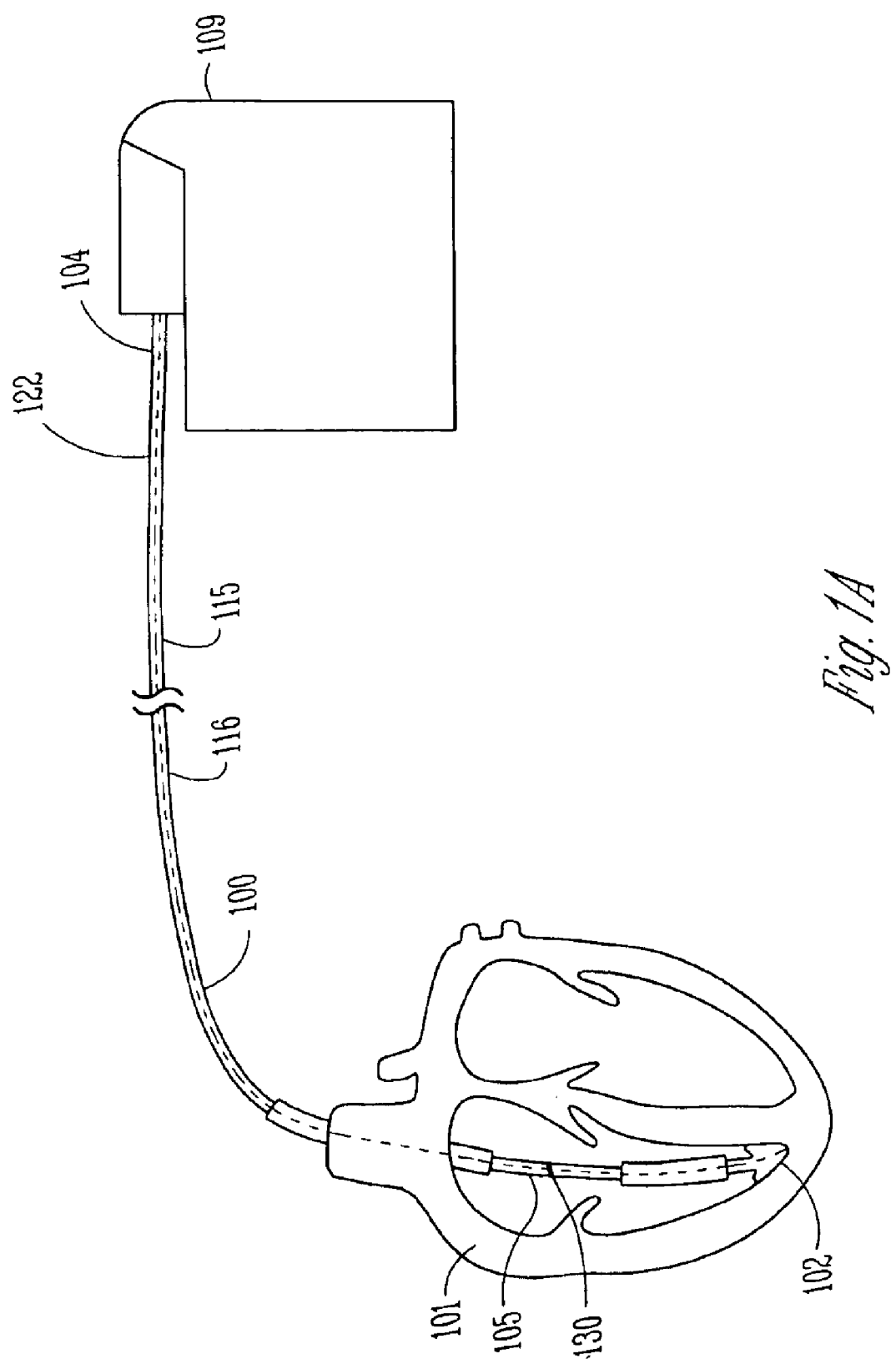
FIG. 1A illustrates a system for monitoring and stimulating the heart constructed in accordance with one embodiment.

FIG. 1A illustrates a single-pass lead 100 for delivering electrical pulses to stimulate a heart 101 and/or for receiving electrical pulses to monitor the heart 101. The lead 100 extends from a distal end 102 to a proximal end 104, and has an intermediate portion 105 therebetween. The distal end 102 is adapted for connection within a patient, the proximal end 104 has a terminal connector which electrically connects the various electrodes and conductors within the lead body to a pulse generator and signal sensor 109. The pulse generator and signal sensor 109 contains electronics to sense various electrical signals of the heart and also produce current pulses for delivery to the heart 101.

The lead 100 includes a lead body 115, an elongate conductor 116 contained within the lead body 115, and at least one electrode 130 coupled with the lead 100. The at least one electrode 130 is electrically coupled with the elongate conductor 116. The lead body 115 is covered with a biocompatible insulating material 122, for instance silicone rubber. The elongate conductor 116 defines a lumen therein and thereby is adapted to receive a stiffening stylet that extends through the length of the lead 100. The stylet is used to stiffen the lead 100, and is manipulated to facilitate the insertion of the lead 100 into and through a vein and through an intracardiac valve to advance the distal end 102 of the lead 100 into, for example, the ventricle of the heart 101. A stylet knob is coupled with the stylet for rotating the stylet, advancing the conductor into tissue of the heart, and for manipulating the lead 100.

Figure 1B:
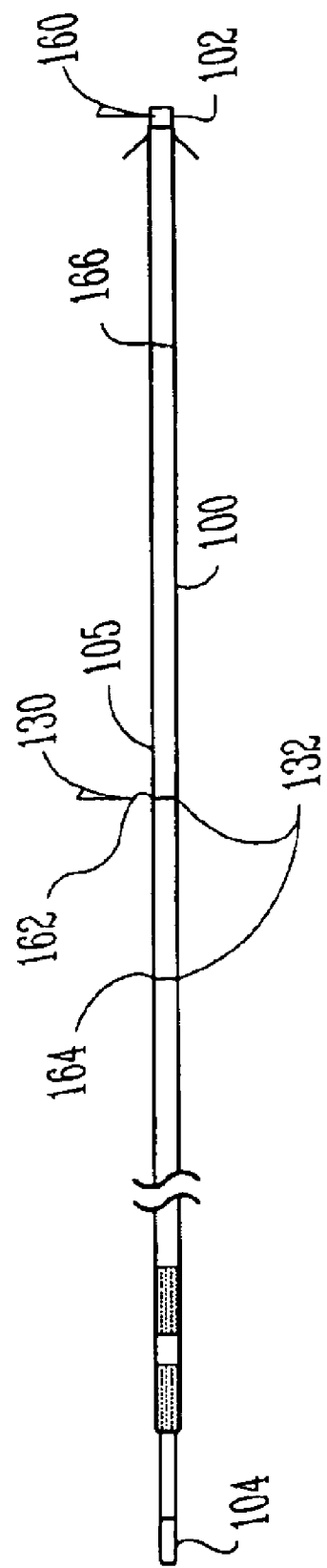
FIG. 1B illustrates a lead including an electrode assembly constructed in accordance with one embodiment.

In one embodiment, as shown in FIG. 1B, the at least one electrode 130 is disposed proximate to the distal end 102 of the lead 100. The distal end 102 of the lead 100, in one embodiment, is disposed within a ventricle of a heart, and the at least one electrode 130 delivers ventricular therapy. The at least one electrode 130 comprises, in one embodiment, a pacing and/or sensing electrode. In yet another embodiment, the at least one electrode 130 is disposed at the intermediate portion 105 between the distal end 102 and the proximal end 104 of the lead 100.

In another embodiment, a plurality of electrodes 132 are disposed on the lead 100. The plurality of electrodes 132 comprise a first electrode 160 disposed at the distal end 102 of the lead, where the first electrode 160 provides ventricular therapy. The plurality of electrodes 132 further comprises a second electrode 162 and/or a third electrode 164. The second and third electrodes 162, 164 are positioned on the intermediate portion 105 of the lead 100 to provide atrial therapy, for example, when disposed within a heart. In yet another embodiment, a fourth electrode 166 is provided on the lead immediately proximal to the first electrode to provide additional ventricular therapy.

FIG. 2 illustrates one embodiment of a lead 200, which includes a lead body 215, at least one electrode 230, and an elongate conductor 280 electrically coupled with the at least one electrode 230. The at least one electrode 230 is used for any or all of the electrodes discussed above. In one embodiment, the at least one electrode 230 comprises a sleeve electrode 210 positioned between insulated lead body sections 216 and 218. The lead body sections 216, 218 partially mask the sleeve electrode 210, leaving an exposed electrode surface 212 which is lesser in surface area than the unmasked sleeve electrode 210. In another embodiment, resistive material other than the lead body 215 is used to partially mask the sleeve electrode 210. The exposed electrode surface 212, in one embodiment, is flush with an outer surface of the lead body 215.

The exposed electrode surface 212 has a significantly smaller surface area than the unmasked sleeve electrode 210. The exposed electrode surface 212, in yet another embodiment, extends about a circumference of the lead body. The impedance of the electrode 230 is controlled by the amount of lead body 215 which masks the electrode 230. To achieve high impedance, the surface area of the exposed electrode surface 212 is reduced by the lead body 215. In one embodiment, the surface area of exposed electrode surface 212 is less than about 1.2 mm$^2$. In another embodiment, the surface area of exposed electrode surface 212 is 0.8 mm$^2$–1.2 mm$^2$. In yet another embodiment, the surface area of exposed electrode surface 212 is about 1 mm$^2$.

In another embodiment, as shown in FIG. 3, the exposed electrode surface 212 is offset from the lead body 215. The exposed electrode surface 212, in yet another embodiment, extends about a circumference of the lead body. The impedance of the electrode 230 is controlled, in one embodiment, by the amount of lead body 215 which masks the electrode 230. In one embodiment, the surface area of exposed electrode surface 212 is less than about 1.2 mm$^2$. In another embodiment, the surface area of exposed electrode surface 212 is 0.8 mm$^2$–1.2 mm$^2$. In yet another embodiment, the surface area of exposed electrode surface 212 is about 1 mm$^2$.

Figure 4:
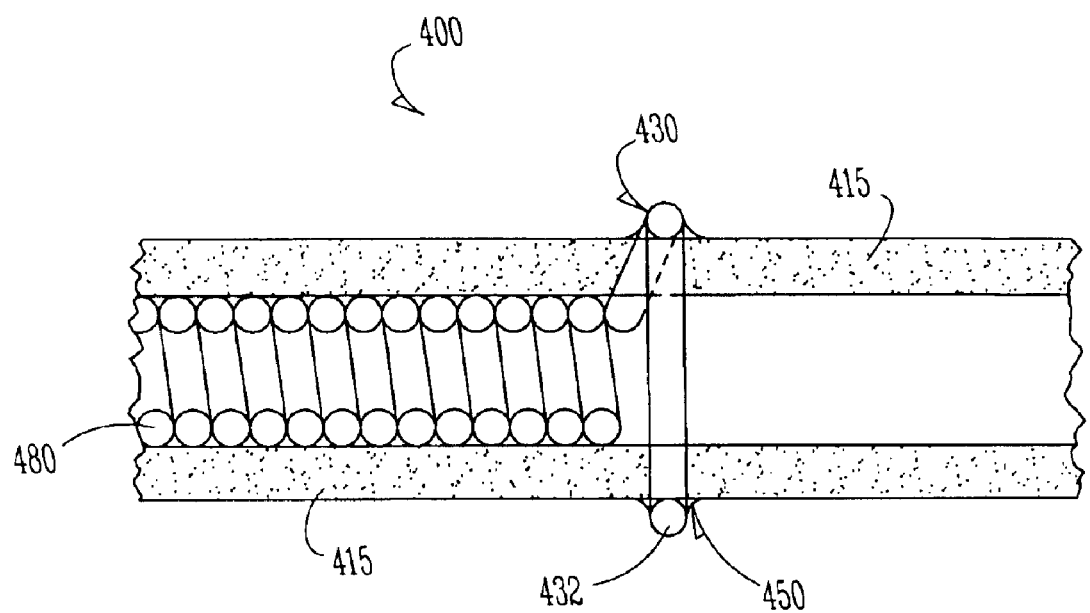
FIG. 4 is a cross-section of an electrode assembly constructed in accordance with one embodiment.

FIG. 4 illustrates another embodiment of a lead 400, which includes a lead body 415, at least one electrode 430, and an elongate conductor 480 electrically coupled with the at least one electrode 430. The at least one electrode 430 is used for any or all of the electrodes discussed above. In one embodiment, the at least one electrode 430 comprises a wire filament 432 is disposed about the circumference of the lead body 415. In one embodiment, the wire filament 432 is partially disposed about the circumference of the lead body 415. The wire filament 432 is electrically coupled with the conductor 480. In one embodiment, the wire filament 432 is formed by extending the conductor 480 through the lead 415, and exposing a portion of the conductor 480 exterior to the lead body 415. In another embodiment, the wire filament 432 is formed of a wire electrically coupled with the conductor 480. The wire filament is coupled with the lead body 415, in one embodiment, using fillets 450.

Figure 5:
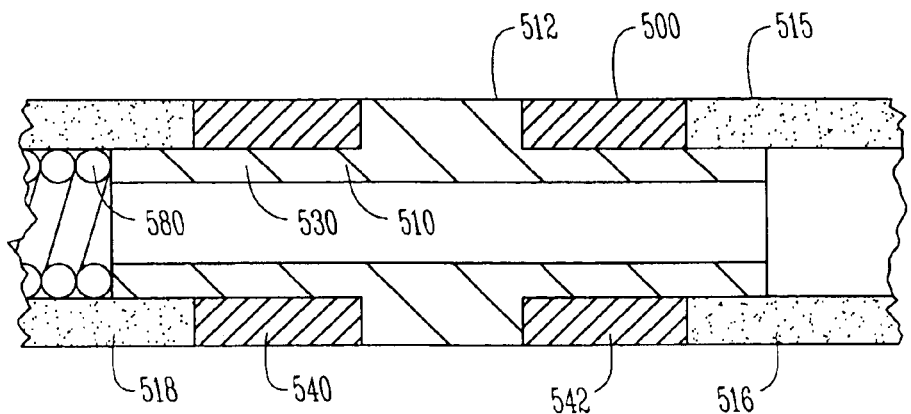
FIG. 5 is a cross-section of an electrode assembly constructed in accordance with one embodiment.

FIG. 5 illustrates one embodiment of a lead 500, which includes a lead body 515, at least one electrode 530, and an elongate conductor 580 electrically coupled with the at least one electrode 530. The at least one electrode 530 is used for any or all of the electrodes discussed above. In one embodiment, the at least one electrode 530 comprises a sleeve electrode 510 positioned between insulated lead body sections 516 and 518. In addition, the at least one electrode 530 includes drug releasing sleeves 540 and 542 which partially mask the sleeve electrode 510, leaving an exposed electrode surface 512. It should be noted that one drug releasing sleeve would also be appropriate to use to partially mask the sleeve electrode 510. The drug releasing sleeves 540, 542, in one embodiment, have an identical composition. One example of the composition of at least one drug sleeve is dexamethasone acetate in a simple silicone medical adhesive rubber binder. Alternatively, the drug releasing sleeves 540, 542 contain different compositions.

The exposed electrode surface 512, in one embodiment, has a significantly smaller surface area than the unmasked sleeve electrode 510. The exposed electrode surface 512, in yet another embodiment, extends about a circumference of the lead body. The impedance of the electrode 530 is controlled, in one embodiment, by the amount of lead body 515 which masks the electrode 530 and/or by the drug releasing sleeves 540, 542. In one embodiment, the surface area of exposed electrode surface 512 is less than about 1.2 $mm^2$. In another embodiment, the surface area of exposed electrode surface 512 is 0.8 $mm^2$–1.2 $mm^2$. In yet another embodiment, the surface area of exposed electrode surface 512 is about 1 $mm^2$. The at least one electrode 530, in one embodiment, is disposed within an atrium of a heart to deliver atrial therapy.

Figure 6:
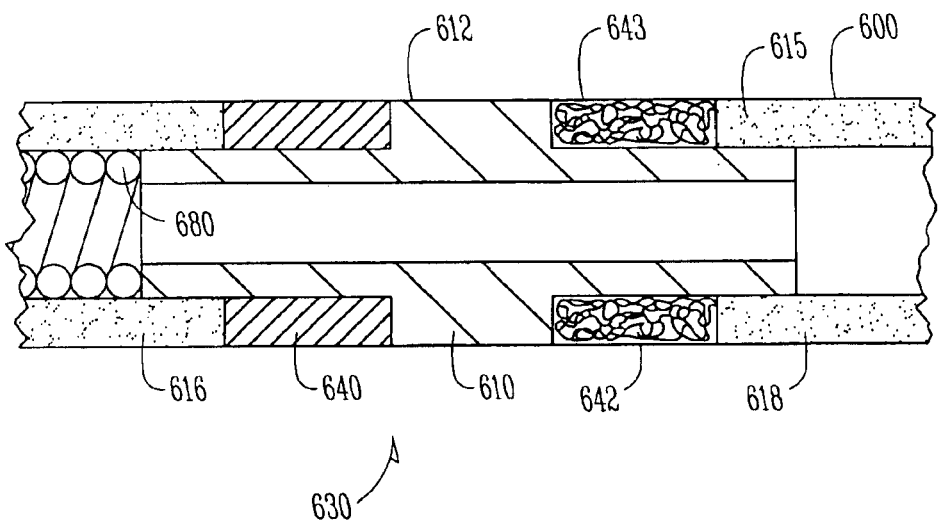
FIG. 6 is a cross-section of an electrode assembly constructed in accordance with one embodiment.

FIG. 6 illustrates yet another embodiment of a lead 600, which includes a lead body 615, at least one electrode 630, and an elongate conductor 680 electrically coupled with the at least one electrode 630. The at least one electrode 630 is used for any or all of the electrodes discussed above. In one embodiment, the at least one electrode 630 comprises a sleeve electrode 610 positioned between insulated lead body sections 616 and 618. In addition, the at least one electrode 630 includes at least one drug releasing sleeve 640 which partially masks the sleeve electrode 610, and leaves an exposed electrode surface 612. One example of the composition of at least on drug sleeve is dexamethasone acetate in a simple silicone medical adhesive rubber binder. Disposed at a position opposite the exposed surface 612 is a porous lead body section 642. The porous lead body section 642 allows for tissue ingrowth. The porous lead body section 642 is provided, in one embodiment, as a porous collar 643 coupled with the lead body 615. In another embodiment, the porous collar 643 includes a drug eluting collar initially containing a water soluble medication, where the medication is released from a collar formed of inert porous binder material. Examples of medication to be used include, although are not limited to: steroid, dexamethasone sodium phosphate, dexamethasone acetate, dexamethasone, antibiotics, or anticoagulation active agents.

The exposed electrode surface 612, in one embodiment, has a significantly smaller surface area than the unmasked sleeve electrode 610. The exposed electrode surface 612, in yet another embodiment, extends about a circumference of the lead body 615. The impedance of the electrode 630 is controlled, in one embodiment, by the amount of lead body 615 and/or drug collar 640 which masks the electrode 630. In one embodiment, the surface area of exposed electrode surface 612 is less than about 1.2 $mm^2$. In another embodiment, the surface area of exposed electrode surface 612 is 0.8 $mm^2$–1.2 $mm^2$. In yet another embodiment, the surface area of exposed electrode surface 612 is about 1 $mm^2$. The at least one electrode 630, in one embodiment, is disposed within an atrium of a heart to deliver atrial therapy.

During use of the lead assembly shown in FIG. 1B, the first electrode 160 disposed at the distal end 102 of the lead provides ventricular pacing and/or sensing, and the second electrode 162 is disposed in the atrium. In one embodiment, the first electrode 160 is cathodic in polarity, and the second electrode 162 is anodic in polarity. In another embodiment, the second electrode 162 comprises a floating electrode. In yet another embodiment, the first electrode 160 is anodic in polarity and the second electrode is cathodic in polarity. The choice of polarity as described alters the effectiveness of the therapy delivered. For example, in a study using a wire filament for an atrial electrode, the bipolar pacing impedance of the lead was at least 708 Ω, and may be as high as 1000–1200 Ω. The higher pacing impedance provided by the lead described and shown in the figures is advantageous in the interest of increasing pulse generator longevity.

Advantageously, the above described lead provides dual chamber pacing therapy delivered by a single lead of simple design which is capable of the high impedance pacing and low threshold. The lead also allows for steroid elution. The high impedance features and the steroid elution increase the longevity of the pacing device since the current drain from the power source is reduced and stimulation thresholds are lowered. The lead uses smaller electrodes which stimulate smaller areas of tissue with high current density, resulting in less energy consumption.

It is to be understood that the above description is intended to be illustrative, and not restrictive. Although the use of the lead has been described for use in a cardiac pacing system, the lead could as well be applied to other types of body stimulating systems. It should be noted that features of the various above-described embodiments may be interchanged to form additional combinations. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead assembly comprising:
   a lead body extending from a proximal end to a distal end, the lead body including a conductor coil disposed therein;
   at least one electrode electrically coupled with the conductor coil and located entirely on an intermediate portion of the lead body between the proximal end and the distal end, wherein the electrode has a surface area less than about 1.2 $mm^2$; and
   a first drug elution collar and a second drug elution collar, wherein the first drug elution collar is disposed proximate to a first side of the electrode and the second drug elution collar is disposed proximate to a second side of the electrode.

2. The lead assembly as recited in claim 1, wherein the electrode has a surface area of .8 $mm^2$–1.2 $mm^2$.

3. The lead assembly as recited in claim 1, wherein the at least one electrode comprises a conductive sleeve partially masked by the lead body, the conductive sleeve having an exposed electrode surface.

4. The lead assembly as recited in claim 1, wherein the intermediate portion is adapted to be disposed within the atrium of a heart, wherein the at least one electrode is disposed on the intermediate portion.

5. The lead assembly as recited in claim 1, wherein the first drug elution collar has a first drug therein, the second drug elution collar has a second drug therein, and the first drug is different than the second drug.

6. The lead assembly as recited in claim 1, further comprising a porous member disposed on the lead body proximate to the at least one electrode.

7. The lead assembly as recited in claim 1, wherein a portion of the at least one electrode is offset from an outer surface of the lead body.

8. The lead assembly as recited in claim 7, wherein the surface area of the at least one electrode extends about a circumference of the lead body.

9. The lead assembly as recited in claim 1, wherein a portion of the least one electrode is flush with an outer surface of the lead body.

10. The lead assembly as recited in claim 1, wherein the at least one electrode comprises an electrode for at least one of pacing and sensing which includes a wire filament disposed about a circumference of the lead body.

11. The lead assembly as recited in claim 10, wherein the wire filament is bonded with the lead body.

12. The lead assembly as recited in claim 1, wherein a portion of the conductor coil extends through the lead body and around the circumference of the lead body.

13. The lead assembly as recited in claim 1, including a second electrode disposed at the distal end of the lead, wherein the second electrode is adapted to be disposed within a ventricle and is adapted to be cathodic in polarity, and the at least one electrode is adapted to be disposed within an atrium and is adapted to be anodic in polarity.

14. The lead assembly as recited in claim 1, including a second electrode disposed at the distal end of the lead, wherein the second electrode is adapted to be disposed within a ventricle and is adapted to be anodic in polarity, and the at least one electrode is adapted to be disposed within an atrium and is adapted to be cathodic in polarity.

15. A lead assembly comprising:

a lead body extending from a proximal end to a distal end, the lead body including a conductor disposed therein;

at least one electrode electrically coupled with the conductor, wherein the at least one electrode includes a conductive sleeve having an exposed electrode surface surrounding the lead body and having an area of less than about 1.2 mm$^2$; and a first drug elution collar and a second drug elution collar, wherein the first drug elution collar is disposed proximate to a first end of the sleeve and the second drug elution collar is disposed proximate to a second end of the sleeve.

16. The lead assembly as recited in claim 15, wherein the first drug elution collar and the second drug elution collar straddle the exposed electrode surface.

17. The lead assembly as recited in claim 15, wherein the first drug elution collar has a first drug therein, the second drug elution collar has a second drug therein, and the first drug is different than the second drug.

18. The lead assembly as recited in claim 15, further comprising a porous member disposed on the lead body proximate to the at least one electrode.

19. The lead assembly as recited in claim 15, wherein the exposed electrode surface is offset from a surface of the lead body.

20. The lead assembly as recited in claim 15, wherein the exposed electrode surface is flush with a surface of the lead body.

* * * * *